United States Patent
Anderson et al.

(10) Patent No.: US 8,425,576 B2
(45) Date of Patent: Apr. 23, 2013

(54) BONE SCREW RETENTION MECHANISM

(75) Inventors: Mark E. Anderson, Irvine, CA (US); Paul A. Munoz, Laguna Beach, CA (US); Janette L. Munoz, legal representative, Laguna Beach, CA (US)

(73) Assignee: WestMark Medical, LLC., Irvine, CA (US)

( * ) Notice: Subject to any disclaimer, the term of this patent is extended or adjusted under 35 U.S.C. 154(b) by 123 days.

(21) Appl. No.: 13/013,669

(22) Filed: Jan. 25, 2011

(65) Prior Publication Data

US 2011/0184415 A1    Jul. 28, 2011

Related U.S. Application Data

(60) Provisional application No. 61/298,437, filed on Jan. 26, 2010, provisional application No. 61/307,278, filed on Feb. 23, 2010.

(51) Int. Cl.
*A61B 17/80* (2006.01)

(52) U.S. Cl.
USPC .......................................... 606/289; 606/294

(58) Field of Classification Search .............. 606/70–71, 606/280–299; 411/121, 166
See application file for complete search history.

(56) References Cited

U.S. PATENT DOCUMENTS

| | | | | |
|---|---|---|---|---|
| 5,578,034 A * | 11/1996 | Estes | | 606/281 |
| 5,741,255 A | 4/1998 | Krag et al. | | |
| 6,331,179 B1 | 12/2001 | Freid et al. | | |
| 6,669,700 B1 | 12/2003 | Farris et al. | | |
| 7,001,389 B1 * | 2/2006 | Navarro et al. | | 606/71 |
| 7,306,605 B2 | 12/2007 | Ross | | |
| 7,909,859 B2 | 3/2011 | Mosca et al. | | |
| 7,931,678 B2 | 4/2011 | Konieczynski et al. | | |
| 2004/0019353 A1 | 1/2004 | Freid et al. | | |
| 2005/0096657 A1 * | 5/2005 | Autericque et al. | | 606/69 |
| 2006/0122602 A1 * | 6/2006 | Konieczynski et al. | | 606/69 |
| 2006/0161157 A1 | 7/2006 | Mosca et al. | | |
| 2006/0200134 A1 * | 9/2006 | Freid et al. | | 606/61 |
| 2007/0055257 A1 | 3/2007 | Vaccaro et al. | | |
| 2008/0294262 A1 * | 11/2008 | Levieux | | 623/17.16 |
| 2008/0300634 A1 * | 12/2008 | Gray | | 606/280 |
| 2009/0118831 A1 | 5/2009 | Trieu | | |
| 2009/0157123 A1 | 6/2009 | Appenzeller et al. | | |
| 2009/0326580 A1 | 12/2009 | Anderson et al. | | |

OTHER PUBLICATIONS

International Search Report of International Application No. PCT/US2011/022575, Filed Jan. 26, 2011.
Keith H. Bridwell, Anterior Cervical Plating, The Textbook of Spinal Surgery, pp. 268-275, Third edition, vol. 1, Wolters Kluwer, Lippincott Williams & Wilkins, Philadelphia, Jul. 11, 2012.

* cited by examiner

*Primary Examiner* — Todd Manahan
*Assistant Examiner* — Eric S Gibson
(74) *Attorney, Agent, or Firm* — Stetina Brunda Garred & Brucker; Lowell Anderson

(57) ABSTRACT

A bone stabilization system is provided having a plate with a top and bottom surface and a hole therethrough extending along a longitudinal axis. An annular groove in the top surface encircles the axis and defines outer facing sides of a plurality of spring members integral to the plate. A plurality of slots define sides of the spring members the inward facing side of the spring members form the upper portion of the hole, which includes a first spherical portion. A fastener with a spherical portion on the fastener head extends into the hole with the spring members urged apart to allow the head to pass but restraining removal until the resistance provide by the spring members is overcome.

25 Claims, 15 Drawing Sheets

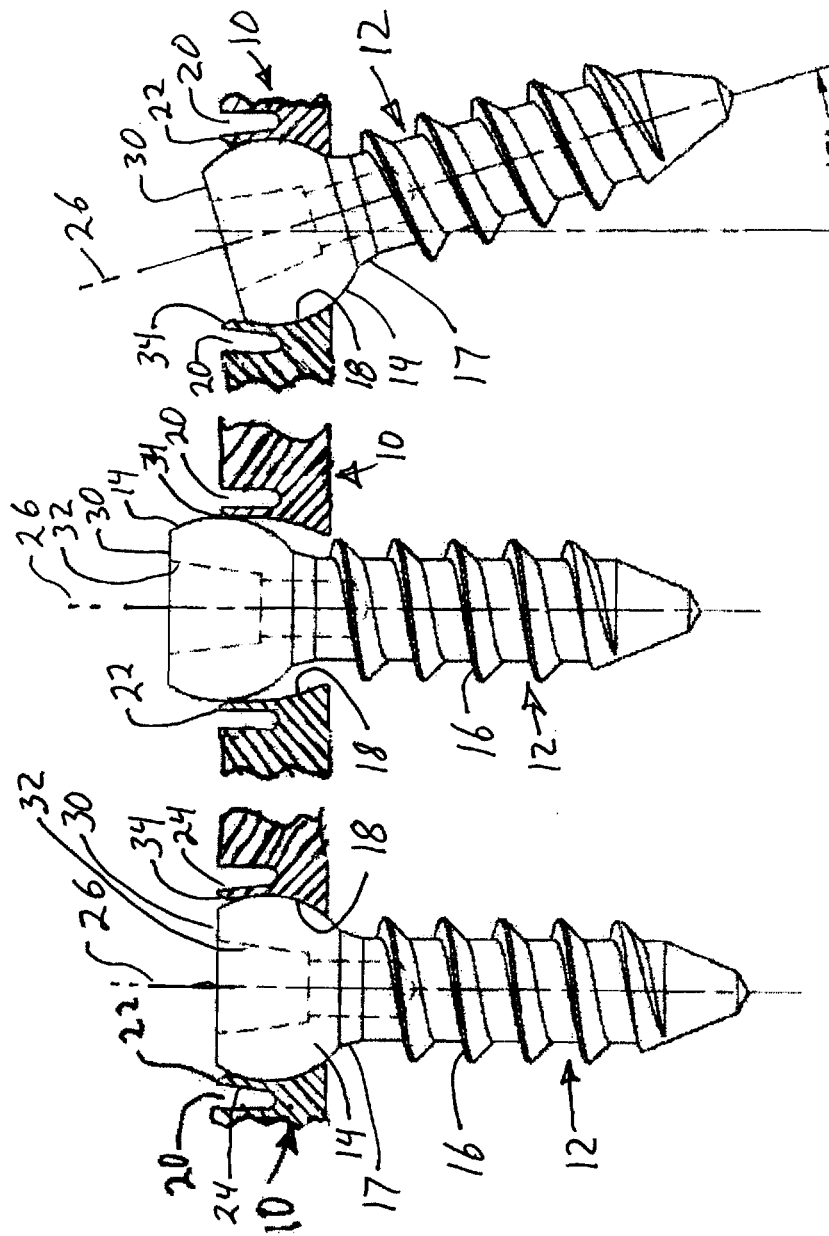

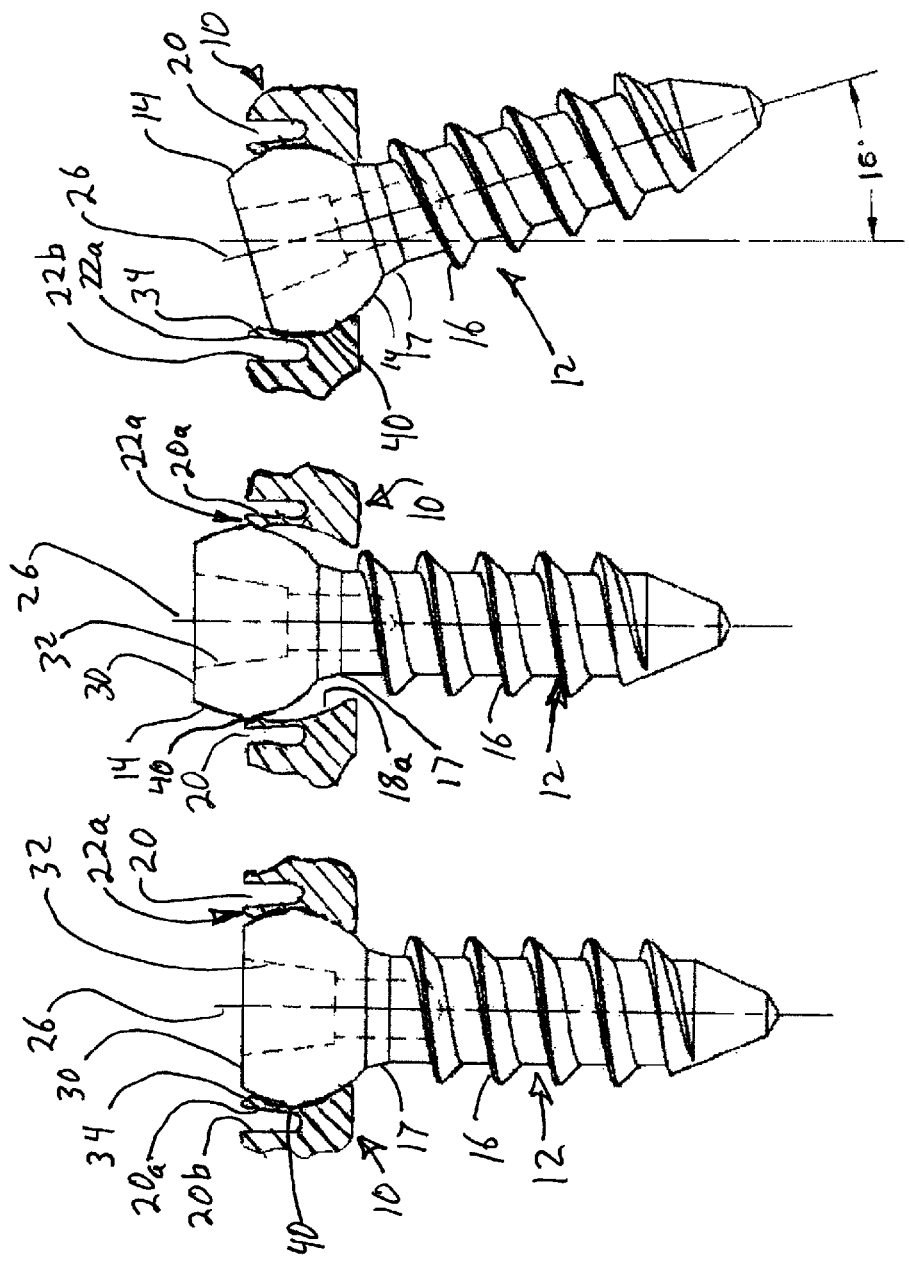

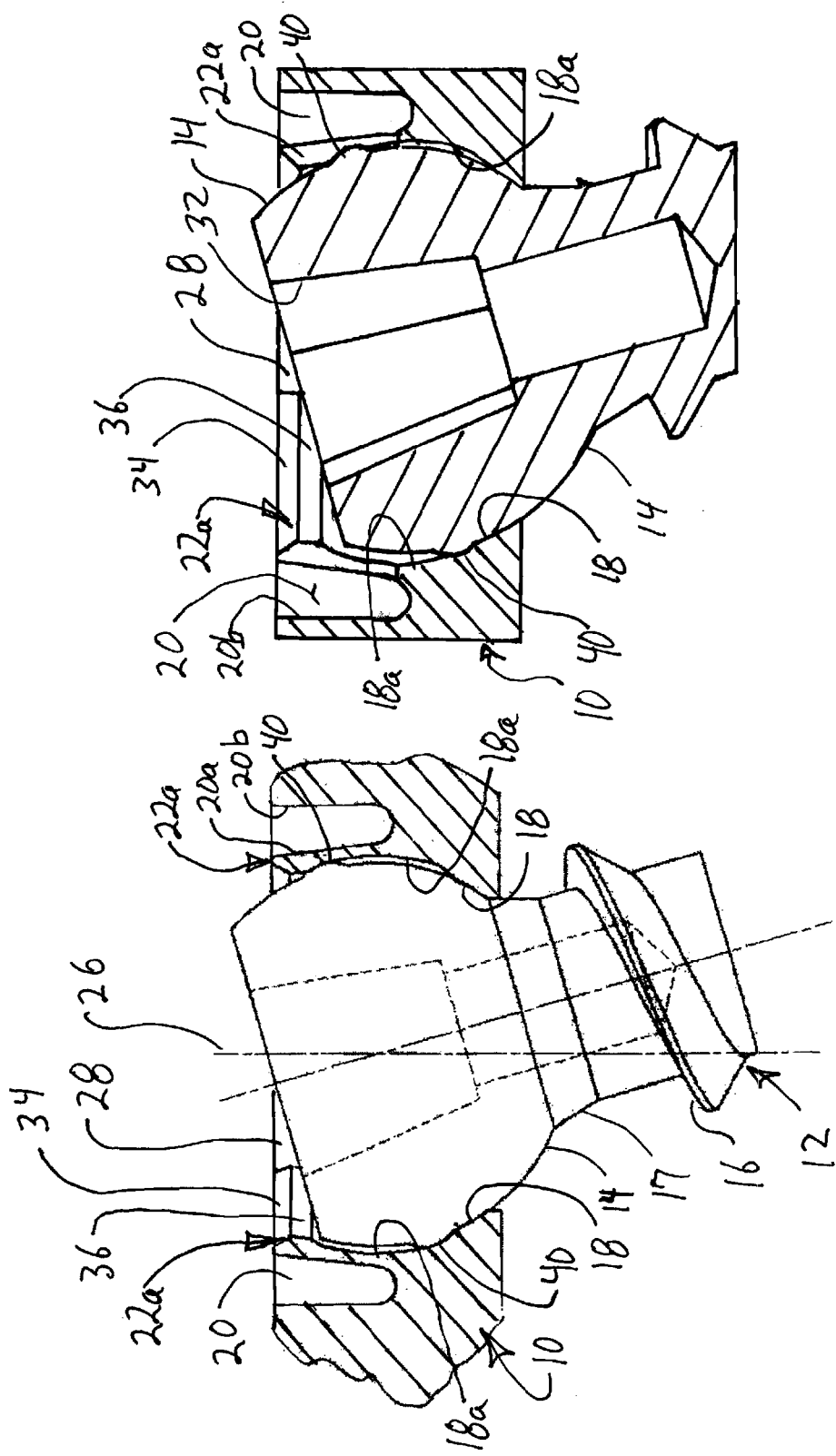

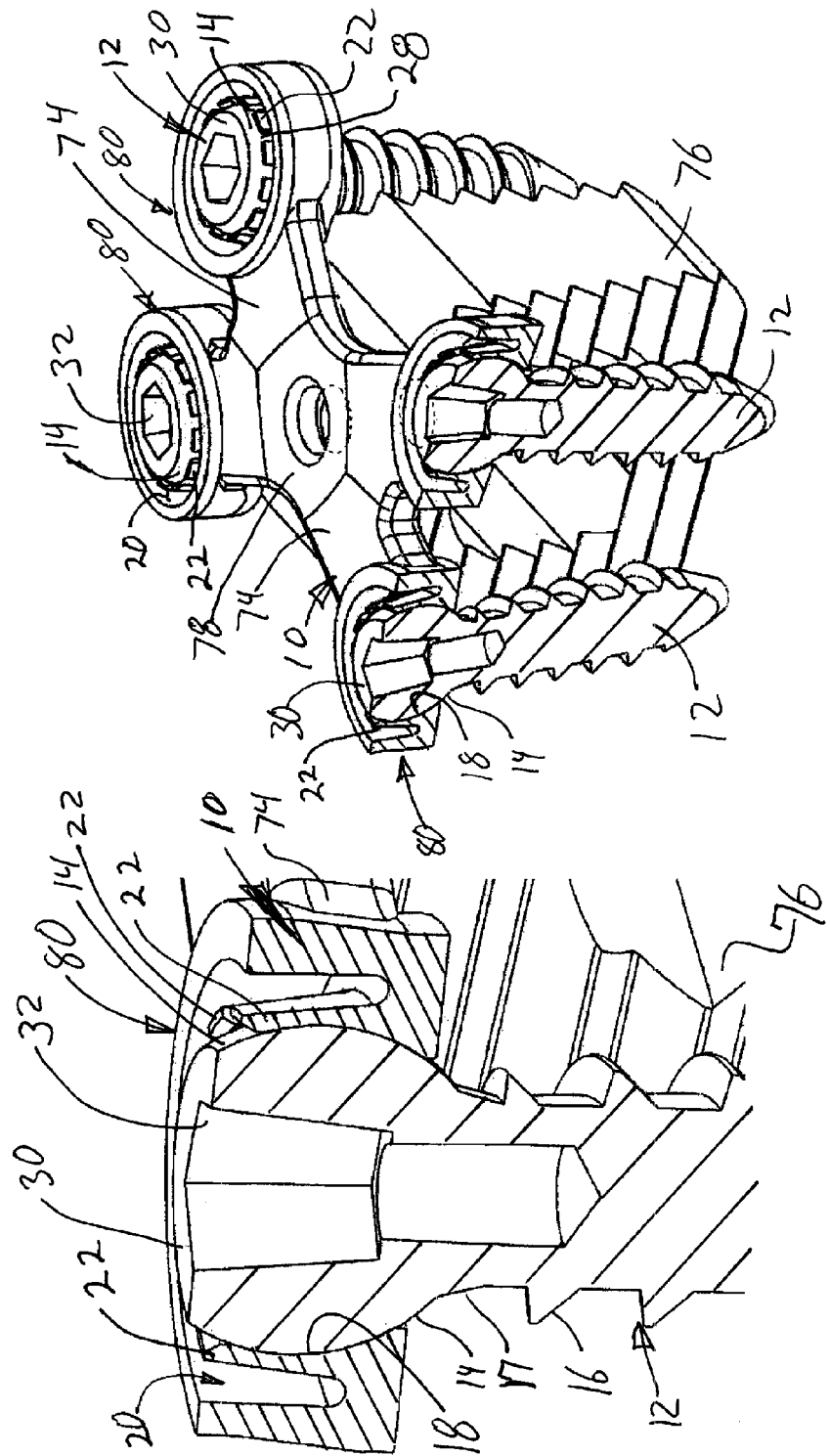

BONE SCREW RETENTION MECHANISM

CROSS-REFERENCE TO RELATED APPLICATIONS

This application claims the benefit of priority under 35 U.S.C. 119(e) to Provisional Patent Application No. 61/298,437 filed Jan. 26, 2010 and Provisional Patent Application No. 61/307,278 filed Feb. 23, 2010, the complete contents of which are incorporated herein by reference.

BACKGROUND

The present invention relates to locking fixation assemblies used in bone fixation and more particularly to screw retention mechanisms.

Bone screws fasten spinal fixation plates and other devices to bones in the human body, or to an animal or mammal body. The fixation plates move and/or flex over time as the bones to which the screws fasten move. The screws can back out of the bone and loosen the strength with which the plate is held to the bone unless the screw is restrained from such movement and/or loosening. Mechanisms to prevent screws from backing out are described in U.S. Pat. No. 6,331,179 to Fried, or application Ser. No. 12/146,291 by Mark E. Anderson et al. But these screw retention devices require formation of a complex bearing or shaped insert that fits into that cavity and that has a complex shapes on both the interior and exterior sides of the bearing or insert. The complexity of making these complex shaped, thin walled structures is undesirable, as are the complexities of installing them. Further, these insert move during installation and use and thus make it more difficult to predict movement and stiffness of the fixation devices during use. There is thus a need for an improved way to retain bone screws.

Prior retention devices using resilient fingers used hooks on the ends of the fingers that hooked over a mating surface on the screw to prevent the screws from unscrewing. But the hooks were small and engaged only a portion of the edge of the screw, so the hooks could break during use, or during removal when the fingers and hooks were pried off the screw, generating debris and causing uncertain screw retention. There is thus a need for a screw retention mechanism that restrains screw back-out and reduces breakage and debris generation.

BRIEF SUMMARY

A plurality of resilient spring members are integrally formed around the opening to a cavity in a bone fixation plate, with the cavity configured to hold the head of a bone screw. The spring members form the upper portion of that cavity and resiliently urge the screw head against unscrewing. The spring members resiliently spread apart to allow the head of the bone screw to enter the cavity and resiliently urge the screw head not to leave the cavity. If the resilient spring force is overcome, the screw can be removed. The spring members are integrally molded as one piece with the plate. Alternatively, the resilient members can be milled, ground and/or cut from the same piece of material as the plate. Additionally, the resilient members can be made separately as an insert or disc that is placed into a cavity in the plate and then permanently secured to the plate as by welding, interference-fit or adhesives.

There is thus provided a bone fixation apparatus in which a threaded fastener passes through a hole in a plate and into a bone to affix the bone to the plate during use. The plate has a hole extending through the plate, with top and bottom surfaces on opposing sides of the plate so that the hole has a circular opening on both surfaces. The bottom surface is adjacent to the bone during use. The openings have a longitudinal axis through the center of the openings. The hole also has a portion of at least a first spherical cavity therein that is also centered on the longitudinal axis. The apparatus further includes a plurality of resilient spring members integrally formed with the plate and encircling the opening on the top surface of the plate. The plate has an annular groove centered on the longitudinal axis and extending a distance into the plate to define a length of the spring members and to further define an outer surface of the spring members facing away from the longitudinal axis. A plurality of slots in the plate extend into the plate about the length of the spring members to define sides of the spring members. The inner side of the spring members facing the longitudinal axis have a curved surface defining a portion of the first cavity. The spring members are configured to move resiliently outwards away from the longitudinal axis to allow a portion of the fastener to be positioned in the cavity, and configured to move resiliently inwards after insertion of that portion of the fastener to resist removal of the fastener from the plate until the resistance of spring members is overcome.

It is preferred that the fastener have a spherical portion on a head of the fastener and have a spherical diameter about the same as that of the cavity or slightly smaller. Further, the inner and outer sides of the spring members are curved with the curves being concentric about the longitudinal axis. Advantageously, the first cavity has a diameter d and the spring members define about half of that cavity.

In further variations, the spring members have an outer surface each of which forms a portion of a cone centered about the longitudinal axis, with the apex of the cone located above the plate during use. The spring members may be formed on a generally cylindrical, annular disc having a slightly conical outer shape coincident with the conical surface on the outer surface of the spring members. The disc may have an outwardly extending flange at the bottom surface of the plate mating with a stepped opening in the plate to position the bottom surface of the disk flush with the bottom surface of the plate.

A distal end of each spring member has a first annular surface oriented to urge the spring members away from the longitudinal axis when the head of a screw passes into the cavity along the longitudinal axis. The first annular surface is preferably conical, with the apex on the longitudinal axis and below the top plate during use. A second annular surface may adjoin the first annular surface and may be further oriented to be generally aligned with the longitudinal axis as the largest portion of a fastener passes the second surface. The second annular surface is preferably conical, with an apex on the longitudinal axis above the plate during use.

In a further variation, the inner side of the spring members may further define a second cavity having a larger diameter than the first cavity, the second cavity extending into the plate below the spring members. The threaded fastener may have a spherical head with a ring extending outward from that spherical head with the ring sized to fit in the second cavity during use, with the second cavity limiting movement of the ring and thus rotation of the screw head and screw. There is also advantageously provided a bone stabilization system having a plate with a top and bottom surface. The plate has a hole therethrough extending along a longitudinal axis. The top surface of the plate has an annular groove centered on the longitudinal axis and extending into the plate a distance sufficient to define outer facing sides of a plurality of spring members integral to the plate. The plate has a plurality of slots defining sides of the spring members. The hole inside the plate has walls defining at least a portion of a first spherical cavity with a diameter d centered on the longitudinal axis. An inward facing surface of the spring members define an upper portion of the first cavity and distal ends of the spring members defining a top opening to the cavity in the top surface of the plate. The plate below the spring members defines a lower portion of the first cavity. The assembly may include a fastener positionable through the top opening. The fastener has a head, with the spring members configured to engage a portion of the head to resist removal of the fastener from the plate during use until the resistance provided by the spring members is overcome.

In further variations of this apparatus, the inward and outward facing sides of the spring members are also curved concentric with the longitudinal axis. The outer facing sides of the spring members may form a portion of a conical surface having an apex on the longitudinal axis and located above the plate during use. The inward facing surface of the spring members may define a portion of a sphere with a diameter of about d. Advantageously, the annular groove has a curved bottom, with the slots extending to about the bottom of the groove.

The hole in the plate may also include a second cavity extending into the walls defining the first cavity and having a diameter D larger than the diameter d. The screw includes a head with a portion of a sphere and an outwardly extending ring on that spherical portion having a diameter of about D, so the ring can move within the second cavity, but is limited in motion by the ends of the second cavity walls. The spring members may each also have a distal end forming a first annular surface inclined to intersect the longitudinal axis below the plate during use. The distal ends of the spring members may also define a second annular surface adjoining the first annular surface and inclined to intersect the longitudinal axis above the top plate.

The plate may be used in various configurations, including an X-shaped spinal fixation plate having four legs with a socket at a distal end of each plate. Advantageously, each socket has the fixation plate described herein.

BRIEF DESCRIPTION OF THE DRAWINGS

FIG. 1 is a partial cross-section showing a portion of a plate with a bone screw retained in a recess in the plate along a longitudinal axis of the recess;

FIG. 2 is a partial cross-section showing the portion of a plate of FIG. 1 with the bone screw partially inserted in the recess;

FIG. 3 shows the plate and bone screw of FIG. 1, with the bone screw inclined at a 15° angle from the longitudinal axis;

FIG. 9 is a partial cross-section of a second embodiment showing a portion of a plate with a bone screw with a protrusion retained in a shaped recess in the plate aligned along a longitudinal axis of the shaped recess;

FIG. 10 is a partial cross-section showing the portion of a plate of FIG. 9 with the bone screw partially inserted in the shaped recess;

FIG. 11 shows the plate and bone screw of FIG. 9, with the bone screw inclined at a 15° angle from the longitudinal axis of the shaped recess;

FIG. 14 is an enlarged portion of FIG. 11 showing part of the plate and screw head inclined at 15°;

FIG. 15 is a view of FIG. 13 showing all parts in cross-section with a cylindrical insert instead of the partial plate;

FIG. 19 is a partial perspective sectional view along 19-19 of FIG. 18;

FIG. 20 is a sectional view along 19-20 of FIG. 18;

DETAILED DESCRIPTION

Figure 4:
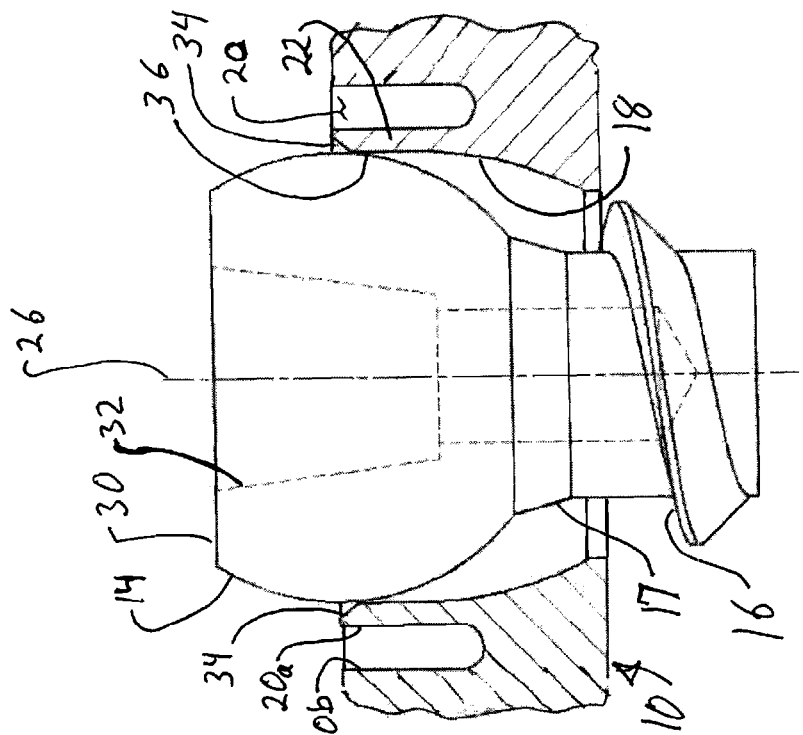
FIG. 4 is an enlarged portion of FIG. 1 showing part of the plate portion and screw head.

The screw retention mechanism is described in connection with a plate 10 used to tie together or fix together two or more adjacent cervical vertebrae C2 through T1, although the screw retention mechanism has general applicability to any device implanted in a mammalian or animal body.

Referring to FIGS. 1-9, 17-20 and 24, the fixation plate 10 can have any desired shape, with an X shape shown for illustration. Exemplary X, H and A shaped plates are described in U.S. application Ser. No. 12/146,291, the complete contents of which are incorporated herein by reference. The X-shaped plate is briefly described in more detail below. Each of the fixation plates 10 has at least one opening through which a threaded fastener 12, such as a bone screw with screw threads 16, passes. The openings have an interior cavity 18 shaped to conform to the shape of a screw head 14. The illustrated embodiments have screw heads 14 with a segment of a sphere with a diameter d. The interior cavity 18 has a matching spherical shape sized to conform to and preferably be slightly larger than the spherical portion of the screw head 14. The bone screw 12 has an optional, self-taping tip, and a tapered neck portion 17 between the shank on which threads 16 are formed and the screw head 14. The neck portion 17 forms an annular surface that can be concave or have a flat inclined surface resembling a portion of a cone with the apex of the cone located downward as viewed in FIGS. 1-3.

An annular groove 20 surrounds each exterior opening in the plate 10 that provides access to the cavity 18 the groove is offset slightly in order to form an encircling ring of spring members, fingers or segments 22. The encircling ring of spring members 22 form a portion of the surface of the cavity 18 in the plate which abut the head 14 of the screw 12 during use. The spring members 22 preferably form an upper portion of the cavity 18, and advantageously extend from about the middle or slightly above the middle of the spherical cavity to the top or exterior of the cavity, preferably flush with the surface of the plate 10 at the cavity 18. The interior surface of the spring members 22 facing the screw head 14 during use thus preferably has a generally circular or generally spherical curve. The spring members 22 are preferably not less than about half the height of the cavity measured along the longitudinal axis 26 which passes through the center of cavity 18. The spring members 22 can be more than half the cavity height.

The spring members 22 flex outward to allow the screw head 14 to enter the cavity 18 but not enough to plastically deform and prevent the members 22 from moving inward to enclose the upper portion of the curved head 14 of the screw 12 to resiliently restrain the screw head from exiting the cavity 18. Preferably, free distal end of each spring member 22 has a flange 24 that is inclined inward toward longitudinal axis 24 of the cavity, along which the screw 12 extends during use. The flanges 24 restrain the screw 12 from backing out during use. Advantageously, the distal flange 24 may be inclined relative to an upper portion of the screw head 14 so that rotating the screw in an unfastening direction will cause the curved portion of the screw head to move the spring members 22 outward. Thus, the spring members exert a resilient force that urges the screw head 14 into cavity 18 to resist removal of the spring, but if that spring force is overcome the flanges 24 are shaped to allow the screw to be unscrewed and removed.

The spring members 22 may be integrally formed from a single piece of material with the plate 10, or forging, or pressure formed power metal or sintered metal. The spring members 22 are advantageously thinnest at the base, which is at the bottom of the annular groove 20. The groove 20 has opposing side walls comprising a smaller diameter, inner side wall 20a and a larger diameter, outer side wall 20b. As used herein, inner refers to a direction toward the longitudinal axis 26, or toward the body along axis 26. Outer refers to the opposite direction. Thus, the spring members 22 have an interior, inner side facing toward longitudinal axis 26 that is at least partially defined by the shape of the cavity 18 and an outer side facing away from axis 26 that is defined by groove 20 and its side wall 20a. Slots 28 separate the spring member 22, with the slots 28 being preferably evenly spaced and extending to the bottom of the groove 20, or to about that bottom. Thus, the cavity 18, groove 20, and slots 28 define the shape and length of each spring member, and the amount of resilient force each spring member resiliently applies to screw head 14 to retain the screw in the plate 10 during use. A retaining force of about 10-15 pounds per screw 12 is believed suitable.

Referring to FIGS. 1-5, the screw head 14 has a spherical outer surface with an optionally flat top 30 truncating the top portion of the screw head. The socket 32 is preferably aligned along longitudinal axis 26. A wrenching socket 32 can be formed in the head 14, with the socket 32 opening onto the top 30. A removal tool (not shown) with a mating surface corresponding to that of socket 32 can be inserted into the socket 32 to tighten or unscrew the bone screw 12.

The spring members 22 are arranged in a circle and define the opening through which the screw head 14 passes to enter the cavity 18. The distal ends of the spring members 22 have an inclined surface 34 (FIGS. 4-5) inclined to abut the lower portion of curved surface of head 14 adjacent the screw shank and spread the spring members 22 apart as the shank of screw 12 passes through the cavity 18 and the head 14 enters the cavity 18. The spring members 22 thus define a first annular surface 34 inclined to facilitate entry of the head 14 into the plate 10 and its cavity 18. The annular surface 34 formed by spring members 22 is preferably conical, and inclined to intersect the longitudinal axis 26 below the top surface of the plate and preferably inside the plate 10. As seen in FIGS. 2 and 5, the spring members 22 are spread apart the greatest distance when the largest portion of the screw head 14 of diameter d passes through the fingers 22.

Figure 5:
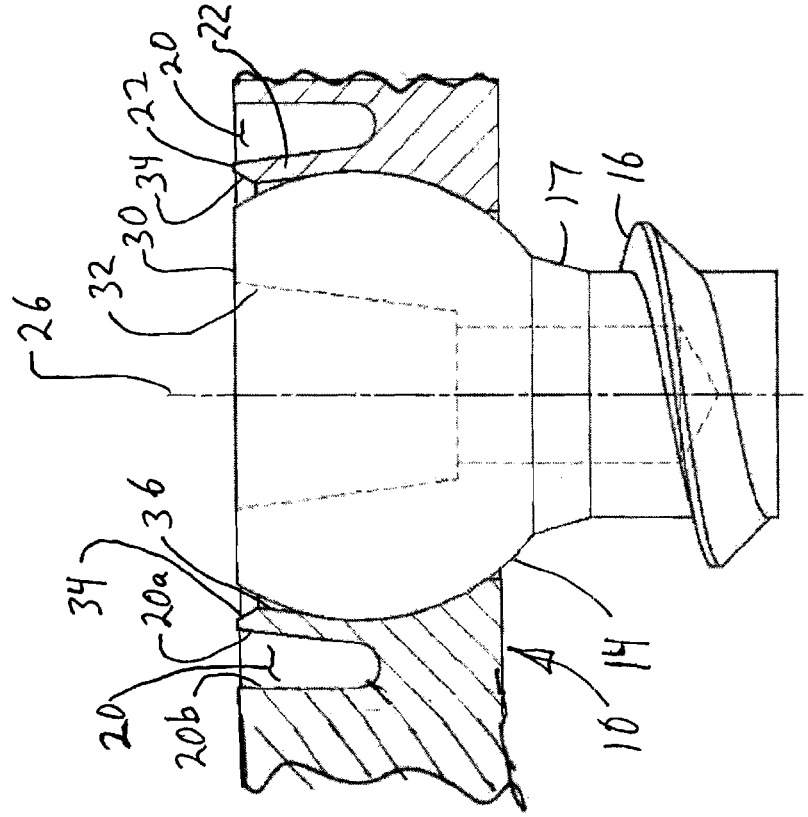
FIG. 5 is an enlarged portion of FIG. 2 showing part of the plate portion and screw head partially inserted.
Figure 7:
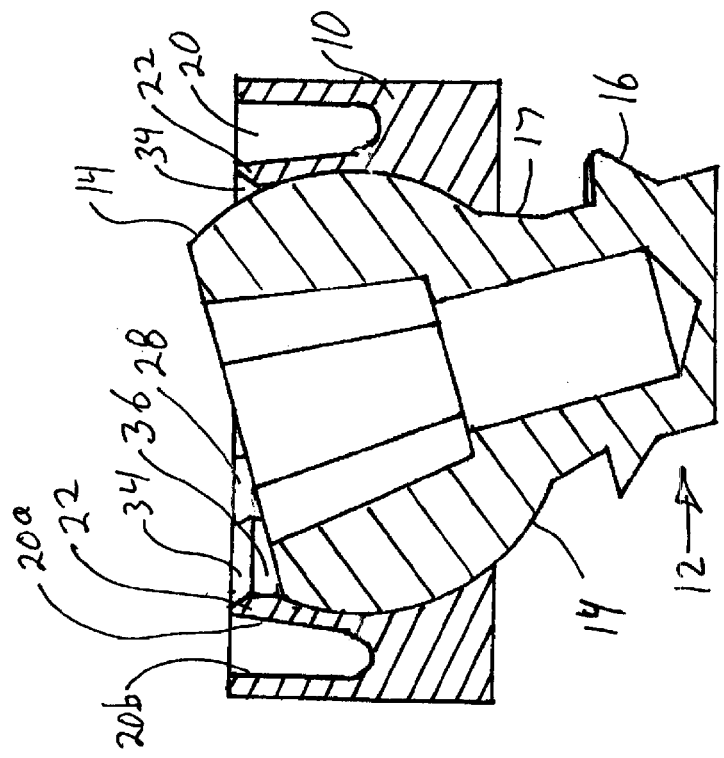
FIG. 7 is a view of FIG. 6 showing all parts in cross-section with a cylindrical insert instead of the partial plate.
Figure 6:
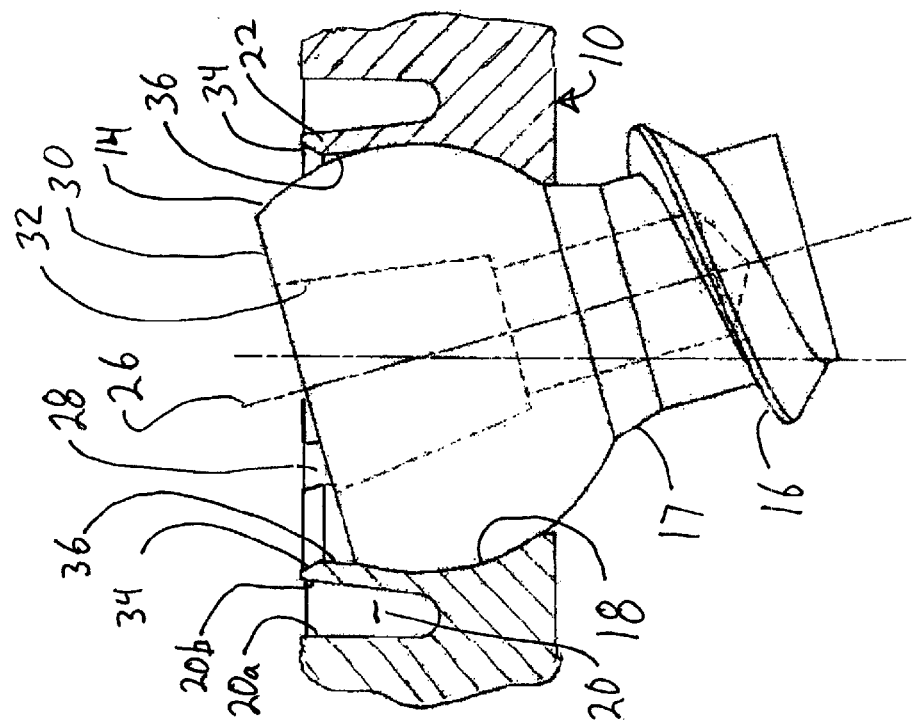
FIG. 6 is an enlarged portion of FIG. 3 showing part of the plate and screw head inclined at 15°.

As seen best in FIGS. 4-6, a flat, non-curved, annular or ring-shaped surface is formed on the distal ends of the spring members 22 adjoining the inclined surface 34. This flat surface 36 is generally parallel to in wall 20a, but may be inclined about slightly 1-5° and preferably about 2-3° to intersect the longitudinal axis 16 above the plate 10 during use. FIG. 5 shows the spherical portion of screw head 14 on the juncture between the inclined surface 34 and the inclined surface 36, and the surface 36 allows head 14 to move downward before engaging the curved portions of cavity 18. The inclined surface 36 also allows the spring members 22 to be thicker and stiffer springs, and reduces the amount which the spring members 22 would have to bend away from axis 26 if the inner surface of spring members 22 were entire shaped to confirm to the spherical head 14 and the flat 36 not used. The flat 36 thus allows variation in the stiffness of retaining spring members 22, and allows stress in the spring members to be lowered.

Referring to FIGS. 1-8 and especially to FIGS. 1-2, as the bone screw 12 is inserted into cavity 18 along axis 26, the lower spherical portion of head 14 abuts the inclined annular surface 34 and forces the spring members 22 to open and allow passage of the screw 12. As the largest portion of screw head 14 passes by the distal ends spring members 22, the spring members are bent outward, away from axis 26, causing a maximum stress condition on the spring members. As the largest portion of screw head 14 passes the annular flat 36 and enters the cavity 18, the spring members 22 are resiliently urged inward toward axis 26 and cooperate with the spherically curved upper portion of screw head 14 to urge the screw 10 downward into the cavity 18. The distal end of each spring member 22 (and 22a) thus has a first annular surface 34 oriented to urge the spring members away from the longitudinal axis 26 when the head 14 of a screw 12 passes into the cavity 18 (or 18a) along the longitudinal axis 26. A second annular surface 36 adjoins the first annular surface 34 and is oriented to be generally aligned with the longitudinal axis 26 as the largest portion of the fastener 12, (i.e., head 14) passes the second surface 36.

When the screw head 14 is seated in the cavity 18 as shown in FIGS. 1 and 4, the inner surfaces of spring members 24 abut the upper portion of the screw head, preferably in an unstressed or slightly stressed condition. The spring members 22 are thus preferably just touching the outer surface of screw head 14, or more preferably, the spring members 22 are slightly bent outward by the head 14 and slightly stressed by that bending in order to exert a resilient force against screw head 14 by spring members 14.

When the bone screw 12 rotates relative to the plate 10 as shown in FIGS. 3 and 6, the spherical portions of head 14 and cavity 18 still engage. Rotations of 15° or more are believed possible with this design. Because the inner surface of cavity 18 and the outer spherical surface of screw head 14 are very close to each other or coincide, such rotation does not alter the resilient force with which spring members 22 abut the head 14 and retain screw 12. As the screw 12 backs out of the cavity 18, the deformation of spring members 22 increases and the retention force applied by the spring members also increases.

Referring to FIGS. 4 and 5, the shape of the groove 20, and in particular the inclination angle of inner wall 20a, reflects the bending of the spring members 22. With the screw head 14 seated in cavity 18 as shown in FIGS. 4 and 6, the inner wall 20a of groove 20 is inclined at an angle of about 5-8° and preferably about 6° to the longitudinal axis 26, inclined to the free, distal ends of members 22 are closer to axis 26 than the bottom portions. When the spring members 22 are spread apart the greatest distance to allow passage of spherical head 14, the inclination of inner wall 20a is about 1-2 degrees relative to the axis 26, with the free, distal ends of the members 22 being further away from the axis 26 and the lower ends which are part of the plate 10. As the bending of spring members 22 increases, the resistance to removal of the screw head 14 increases, and the stress on the bent spring members 22 increases. For plates 10 and spring members 22 made of titanium alloy such movement is believed suitable without plastically deforming the spring members. The particular dimensions and angles of bending will vary with the materials used. Titanium alloy Ti-6A1-4V is believed suitable.

Figure 8:
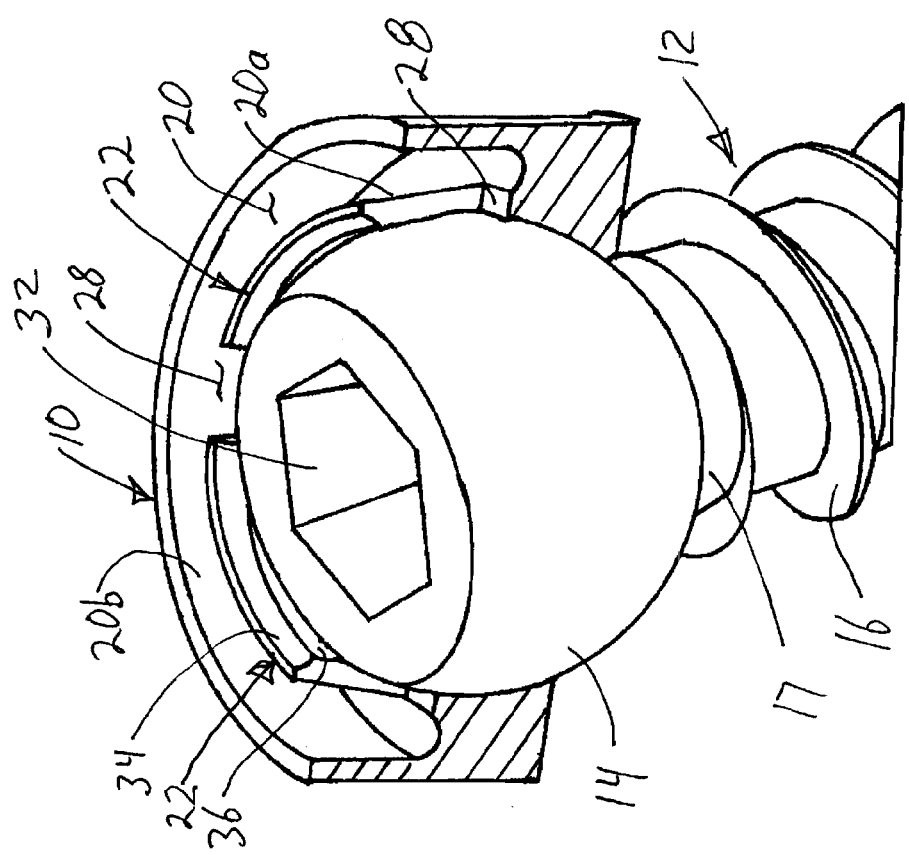
FIG. 8 is a perspective view of FIG. 7.

From 6 to 18, possibly more, spring members 22 may be used. Using four spring members 22 is makes it difficult to elastically deform the members when inserting and removing the screw head 14. From 5 to 14, equally spaced spring members are believed suitable, while 10-12 spring members, equally spaced, are believed preferable. It is believed the gaps between spring members 22 may be about the same as the width of the members, or smaller. As the number of spring members 22 decreases, the stress increases and the retention force increases. As the number of spring members 22 increases, the retention force decreases, the stress lowers, and the manufacturing complexity increases. For example, FIG. 8 shows two of four spring members 22, while FIGS. 17-20 show more. As the number of springs increases, and the curvature of each spring member 22 increases, and bending such a curved member sufficiently to allow insertion and removal of the spherical portion of head 14 creates stress problems and plastic deformation with the spring members 22. Thus, this figure is more useful to understand the design configuration and operation rather than reflect the number of spring members 22 used.

Referring to FIGS. 4-8, 18-20 and 24, the cavity 18 has a spherical shape with a diameter of about d to allow rotation of the spherical screw head 14. The cavity 18 has a bottom portion formed in the plate 10, and an upper portion formed by spring members 22. The bottom portion of cavity 18 formed in the plate 10 has a continuous, spherical surface. The upper portion of cavity 18 is formed by spring members 22 which form a sphere with a diameter d that is about the same as the diameter of the spherical head 14. The spring members 22 have a lower portion adjacent the bottom of plate 10, which lower portion is spherical to conform to the shape of the abutting portion of head 14 during use. That spherical shape at the lower portion of the spring member 22 turns into a straight portion 36, which mates with outwardly inclined portion 34 at the free, distal end of each spring member 22. The outer portion of spring members 22 are formed by curved and inclined surface 20a, resembling a truncated cone, separated by gaps or slots 28 separating adjacent spring members 22. The gaps or slots 28 between the adjacent spring members 22 cause the spring members to provide a discontinuous spherical surface on the upper portion of the cavity 18.

Figures 12, 13:
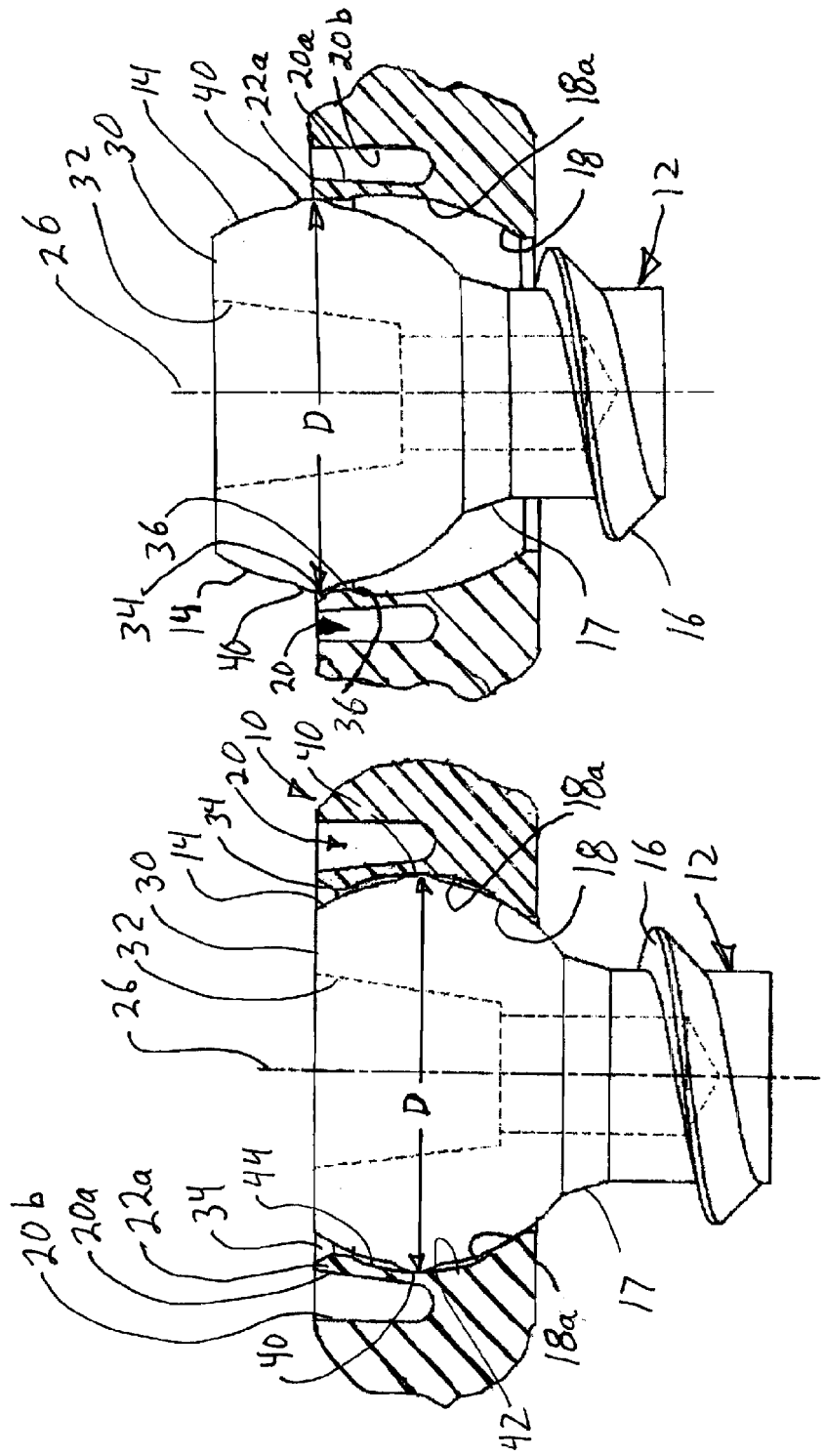
FIG. 12 is an enlarged portion of FIG. 9 showing part of the plate portion, shaped recess and the protrusion on the screw head.
FIG. 13 is an enlarged portion of FIG. 10 showing part of the plate portion and screw head partially inserted into the shaped recess.

Referring to FIGS. 9-16, 18-21-23 and 25, a second embodiment is shown in which the bone screw 12a has a motion limiting ring 40 that fits into a groove 42 (FIG. 12) formed by a plurality of recesses 44 in each of the inward facing surface of spring members 22a and an annular recess in the walls of the plate 10 forming or defining cavity 18a. The remainder of the screw 12a and plate 10 are as previously described and will not be repeated here.

The motion limiting ring 40 may be continuous or intermittent, and preferably comprises a raised or protruding ring located in a plane through the center of the screw head 14a and orthogonal to the longitudinal axis 26. When the bone screw 12 is vertical as in FIGS. 9 and 10, the ring 40 is located at the maximum diameter of the spherical outer bearing surface of the screw head 14a, and extends the maximum diameter of that screw head 14a. The motion limiting ring 40 is shown with a curved cross-section, preferably a semi-circular. The ring 40 forms an annular raised surface extending around the periphery of the screw head 14a, and as described later, serves to limit motion of the screw relative to the plate 10. The maximum diameter of the screw head 14a at the location of the ring 40 is a diameter D, which is larger than the diameter d of the spherical screw head 14a without the ring 40, and larger than the diameter of the cavity 18a without the recessed groove 42 formed in the walls defining the cavity 18a.

The groove 42 has an upper portion formed in the spring members 22a. The inward facing surface of the spring members 22a, the surface facing axis 26, has a recess 44 formed therein with the recess 44 shaped to form a portion of a spherical surface about the same as diameter D or slightly larger. The groove 42 does not extend all the way to the openings in the top and bottom surfaces of plate 10 in which the cavity 18a is formed, and thus recess 44 does not extend all the way to the free, distal end of spring members 22a. The groove 42 has a lower portion formed in the plate 10, below the spring members 22a. That lower portion also has a spherical diameter of about D or slightly larger. The groove 42 does not extend to the opening in the lower surface of the plate 10 which opening allows access to cavity 18a.

Figure 25:
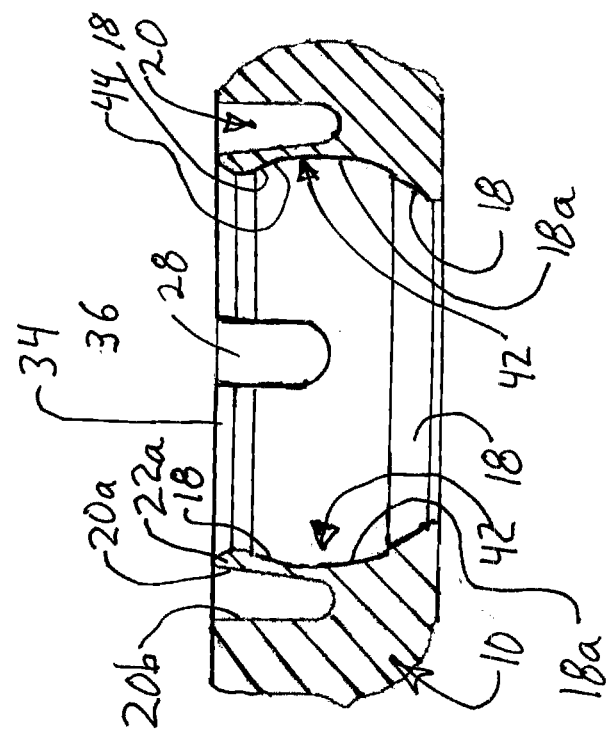
FIG. 25 is a partial sectional view of the plate and cavity of FIG. 9 without a screw.
Figure 24:
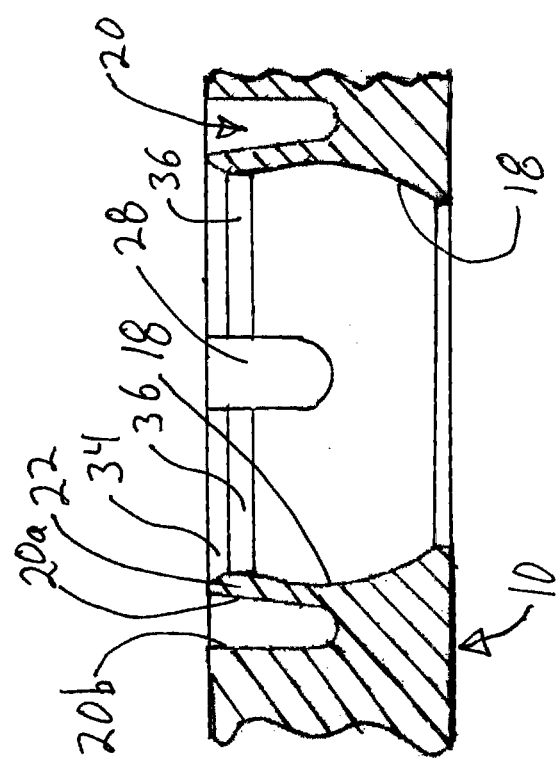
FIG. 24 is a partial sectional view of the plate and cavity of FIG. 1 without a screw.

As best seen in FIGS. 14-15 and 25, the cavity 18 in the plate 10 has a shape formed by spheres of two different diameters. Cavity 18 opens onto the top and bottom surfaces of the plate 10 in which the cavity is formed. The edges of the cavity 18 adjacent the top and bottom surfaces of plate 10 form annular portions of a spherical cavity 18 with a diameter of about d. The upper portion of cavity 18 is discontinuous because of the gaps 28 between the spring members 22a that define the upper portion of the cavity, while the portion of cavity 18 adjacent the lower surface of the plate 10 is continuous. The middle portion forming cavity 18a has a groove 42 extending around the entire circumference of the cavity with curved walls defining a portion of a sphere of diameter D. The cavity 18a thus has groove 42 forming a second spherical surface of diameter D, with the recesses 44 in spring members 22a forming the upper portion of that second spherical surface. The gaps between spring members 22a form a non-continuous second spherical surface of diameter D in the upper portion of the cavity 18a. The lower portion of second cavity 18a is formed in the plate 10 and has a continuous surface. The cavity in the plate 10 thus has a first spherical cavity 18 of smaller diameter d about the same as the diameter of spherical head 14a on bone screw 12. The cavity in the plate 10 has a second, larger spherical cavity 18 of a diameter about D, corresponding to the outer periphery of the motion limiting ring 40. The cavities 18, 18a have the same center, located on axis 26, with the second cavity formed by the curved walls of annular groove 42. The inner side of the spring members 22a thus further define a second cavity 18a having a larger diameter than the first cavity 18, with the second 18a cavity extending into the plate 10 below the spring members 22a.

Referring to FIGS. 9-16 and especially to FIGS. 9-10, as the bone screw is inserted into cavities 18, 18a along axis 26, the lower spherical portion of head 14a and the lower portion of ring 40 abut the inclined annular surface 34 and force the spring members 22a to open and allow passage of the screw 12 and ring 40. As the ring 40 passes through the spring members 22a, the spring members are bent outward, away from axis 26, causing a maximum stress condition on the spring members. As the ring 40 passes the annular flat 36 and enters the second cavity formed by groove 42, the spring members 22a are resiliently urged inward toward axis 26 and cooperate with the spherically curved upper portion of screw head 14a to urge the screw 10 downward into the cavity 18, 18a.

When the screw head 14a is seated in cavity 18 the spherical head 14a abuts or almost abuts cavity 18 at the top and bottom of the plate 10 in which the cavity 18 is formed. The motion limiting ring 40 is then located in the second cavity 18a formed by groove 42. The center of rotation of the screw head 14a, ring 40 cavity 18 and cavity 18a are at the same location—within acceptable manufacturing tolerances. As the screw 12 rotates the head 14 and ring 40 also rotate. The ring 40 centers the screw within cavity 18a and locks against the cavity walls when the diameter of the ring 40 exceeds the diameter of the walls of the cavity abutting the ring to prevent the screw 12 from passing further through the cavity 18, 18a. Preferably, the lower portion of cavity 18 also abuts the screw head 14a to also stop movement of the screw. Thus, the screw head 14 and its ring 40 may abut the walls of both cavities 18, 18a to limit movement of the screw along axis 26 and to secure hold the plate 10 against the bone into which the screw 12 is embedded.

As the ring 40 rotates or tilts toward its extreme angles of rotation, the position limiting ring reaches opposing upper and lower edges of groove 42 which forms the second cavity 18a, and begins to bend the spring members 22a outward. The resulting bending of the spring members 22a exerts a motion limiting force on the ring 40 which resiliently urges the screw head into an orientation with the ring 40 within the groove 42 and second cavity 18a. The ring 40 in groove 42, cooperating with spring members 22a, provide means for resiliently restraining rotation of the screw 12 away from the longitudinal axis through cavity 18, 18a. Alternately phrased, the identified parts resiliently restrain rotation of the screw 12 in directions orthogonal to the axis 26.

In addition to limiting rotation of the screw 12 orthogonal to axis 26, the spring members 22a cooperate with abutting portions of screw head 14 and ring 40 to stop back out of the screw. As the screw head 14 and ring 40 are unscrewed, those parts must force spring members 22a to bend outward, away from axis 26, causing the spring members 22a to exert a force against the screw 12 which restrains back-out of the screw 12.

The spring members 22, 22a and the cavity 18, 18a, groove 20 and slots 28 which define the spring members can be integrally molded as one piece with the plate, and as needed ground or machined to final dimensions. Alternatively, the spring members 22, 22a, cavities 18, 18a, groove 20 and slots or gaps 28 can be cast, cut, milled, ground or otherwise formed from the same single piece of material as the plate 10. The bottom of the groove 20 is preferably rounded by casting or grinding in order to reduce stress concentration. The interior of cavity 18, 18a is also preferably ground to the final dimensions in order to provide a smooth surface, with the formation or cutting of slots 28 preferably occurring after the cavity or cavities are formed. The bottom of slot 20 is preferably ground with a ball grinder in order to produce a curved surface joining the spring members 22, 22a and plate 10 in order to reduce stress and reduce potential cracking and breakage. Spring members 22, 22a formed by the above methods are integrally formed with the plate 10 containing cavity 18.

While it is preferred that cavity 18a be formed of two cavities of differing diameter, it need not be so. Cavity 18a could be a single diameter about D, large enough to accommodate ring 40 rotating within the cavity. Similarly, as shown in FIG. 25, the cavity 18a could have the larger spherical cavity 18 at the lower portion of the plate 10, with the cavity 18a extending from the lower portion of plate 10 into inward facing portion of the segmented spring members 22a, and with no portion of cavity 18 formed in the spring members.

Figure 16:
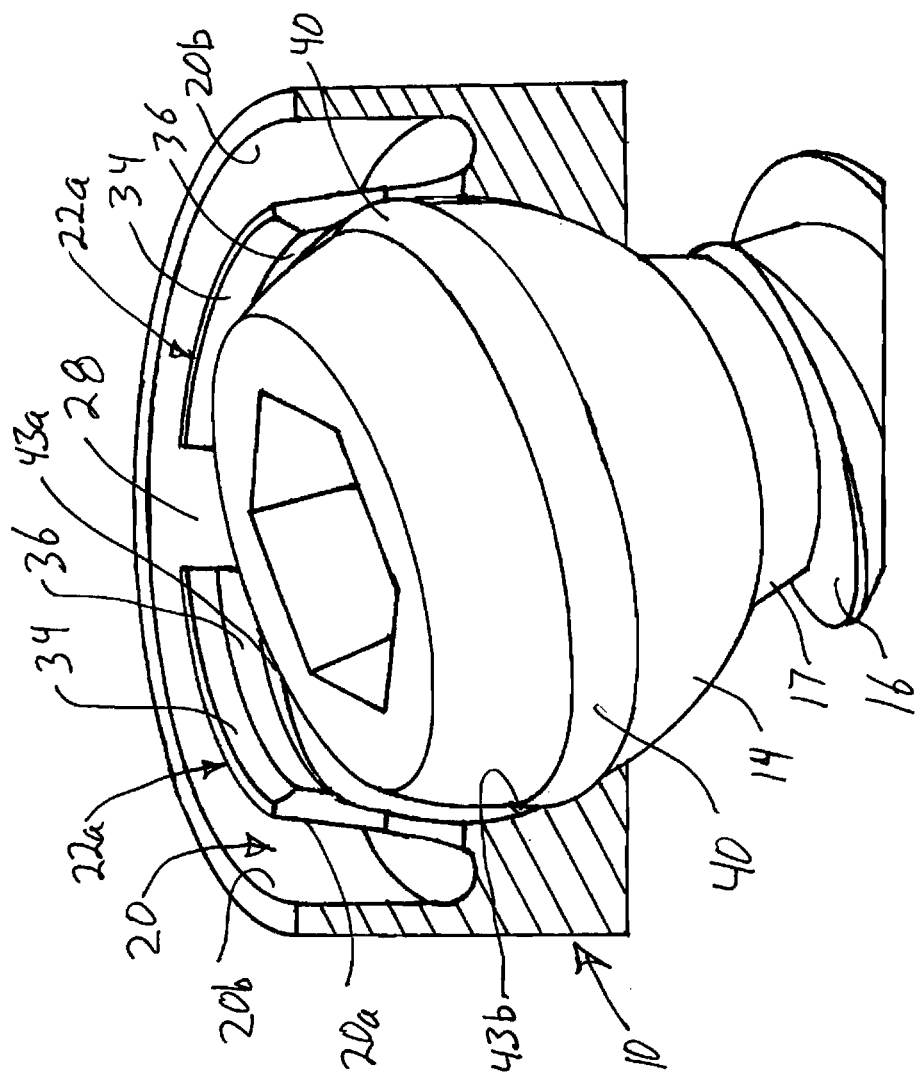
FIG. 16 is a perspective view of the screw head shown FIG. 15 and the cylindrical insert.
Figure 17:
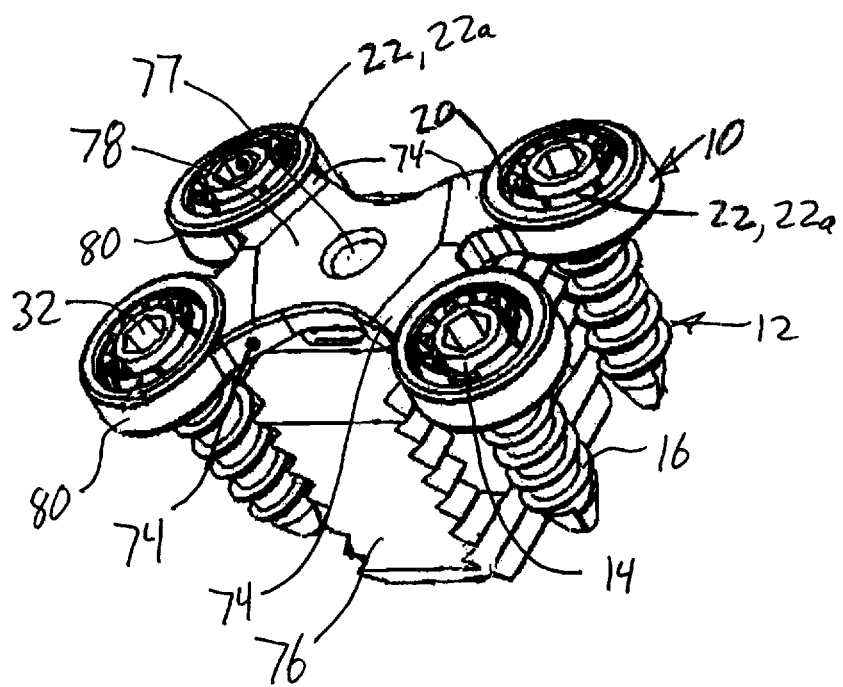
FIG. 17 is a perspective view of a spinal fixation plate with an X shape and four cavities containing the screw retention mechanisms of this invention, with screws inserted.

Referring to FIG. 16, the groove 42 can be formed entirely by the segment of the second cavity 18a, or it can have one or more transition surfaces 43a, 43b. Thus, the juncture between the first and second cavities, 18, 18a, respectively, may be formed by a first transition surface 43a comprising an annular, conical surface with the inclination angle selected based on the abruptness with which the tilting of ring 40 and screw 12 is to stop. Thus, adjoining the annular surface 36 on spring members 22a could be another inclined transition surface 43a, having a conical shape with the apex located on axis 26 above the plate 10, with the other side of that inclined transition surface 43a adjoining the second cavity 18a. At the lower end of the cavity 18a could optionally be located a second transition surface 43b that is advantageously conical and formed in the body of plate 10. The second conical transition surface 43b has an apex on axis 26 located below the bottom of plate 10 or within the lower portion of plate 10. The second transition surface 43b adjoins cavity 18 at the lower end of the plate 10. In this variation the groove 42 includes the upper (conical) transition surface 43a, cavity 18a, and the lower (conical) transition surface 43b adjoining the cavity 18a and cavity 18. The two conical transition surfaces 43a, 43b have apexes on opposite sides of the middle of plate 10. The inclined, conical surfaces 43a, 43b are believed preferable for the transition surfaces, but concave curved surfaces are also believed suitable.

Figure 26:
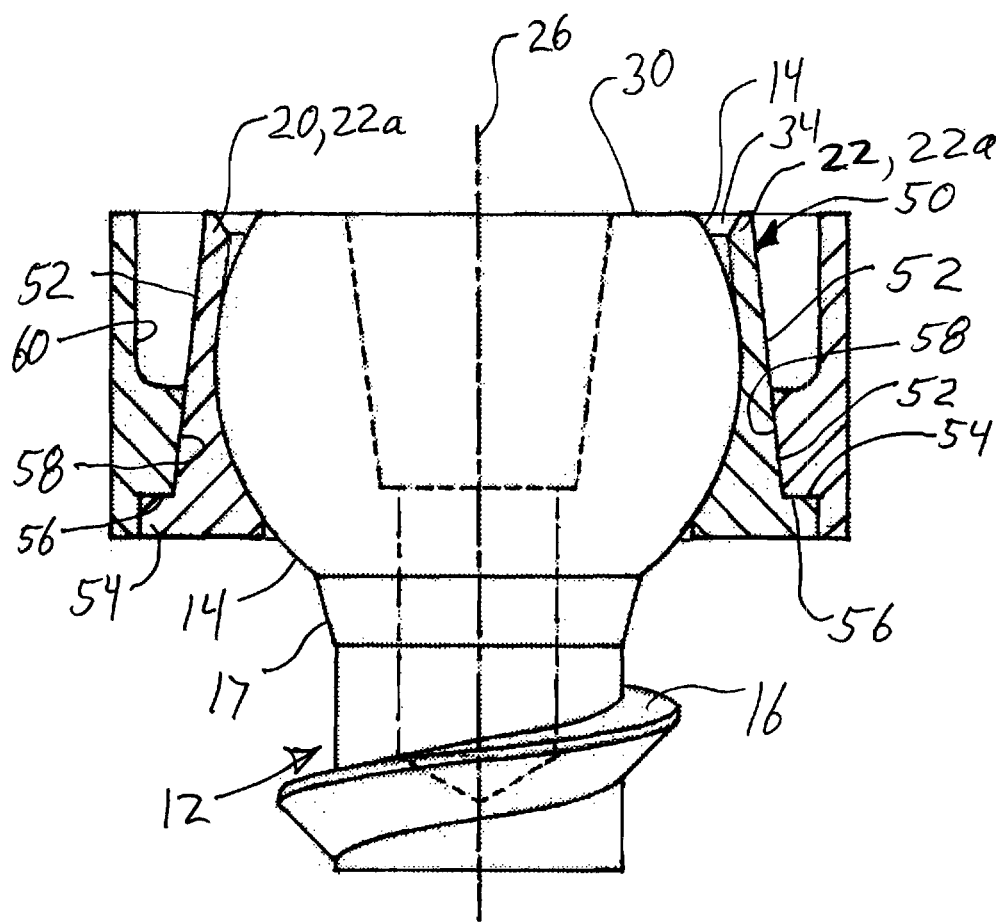
FIG. 26 is a sectional view of a further embodiment showing a disc containing spring members in a portion of a spinal fixation plate.

Referring to FIG. 26, the result of a further manufacturing method is shown in which the resilient members 22, 22a are formed in a disc which is then affixed to a mating hole in the plate 10 or into a mating part which in turn forms an insert affixed to a mating hole in plate 10. The disc 50 may resemble an annular ring with an outer surface 52 and outward extending flange 54 at the bottom of the disc. The flange 54 abuts a mating recess 56 in the bottom of plate 10 to position the disc in the plate 10 along the length of axis 26. The outer surface 52 is shaped to fit pass thorough and fit into a correspondingly configured hole in the plate 10 shaped to receive the disc 50, and preferably to form a press fit or interference fit with a portion of the disc so as to form an integral part with the plate 10. Alternatively, the disc 50 can be fastened by adhesives, welding or other permanent fastening mechanisms and methods to form an integral part with the plate 10.

The disc 50 has spring members 22, 22a formed on an upper portion of the disc. The outer surface of the spring members may be curved as described above. But preferably the outer surface 52 of the spring members 22, 22a and of the disc 50 is conical and inclined at an angle of about 7° from the vertical in FIG. 26, although the angle can vary. The disc 50 has slots 28 separating the spring members 22, 22a. Thus, the spring members 22a have an outer surface facing away from longitudinal axis 26, with the outer surface of each spring member 22a forming a portion of a cone centered about the longitudinal axis. The inclination of the conical sidewalls converges on the longitudinal axis 26 above the head 14 of the screw 12 and away from the bone to which the plate 10 is fastened.

The disc 50 has a continuous, solid bottom portion, with an interior cavity 18, 18a as discussed above. For ease of illustration, only cavity 18 is shown in FIG. 28. The disc 50 has a longitudinal axis coincident with axis 26 and except for the possible number of spring members 22, 22a, is preferably symmetric about axis 26. The flange 54 extends outward from the bottom of the disc 50. A flange 54 extending outward from the conical surface 52 about 0.1 inches or less is believed suitable, but the flange length can vary. A circular periphery on the flange 50 and outer surface 52 is preferred.

The plate 10 may have a hole configured to receive the disc 50 and thus has a stepped recess 56 configured to mate with flange 54 and form a generally flat surface extending across the juncture of the bottom of the plate 10 and disc 54. The stepped recess 56 is preferably circular to correspond with the preferred shape of flange 54, but the recess shape will preferably vary to correspond with the shape of the flange 54. The hole through the plate 10 has an inclined conical sidewall 58 configured to allow spring members 22, 22a to pass while forming an interference fit with the non-slotted, lower portion of the disc 50. The inclination of sidewall 58 corresponds to that of the outer surface 52 but one or both of the outer surface 52 or inclined sidewall 58 is inclined to create an interference fit along the sidewall 58. The inclined sidewall 58 has a lower end adjacent the stepped recess 56 and an upper end at a location at or near to the bottom of slots 28 during use. The hole in the plate 10 may have an upper recess 60 extending located to form the annular groove 20 when the disc is inserted into the hole in the plate. The upper recess 60 extends from the top surface of plate 10 to the upper portion of inclined surface 58, and forms an annular space between the plate 10 and the spring members 22, 22a. The result depicted in FIG. 26 is an annular groove 20 having one curved corner on the outer edge of the bottom of the groove and one sharp corner on the inner edge of the bottom of the groove formed by the intersection of the outer surface 52 of the disc and the bottom of the groove.

In use, the disc 50 is formed with cavity 18, 18a formed inside of the disc, using one of the above described methods. The disc 50 is then press fit into side walls 52 of plate 10, with flange 54 preventing passage through the hole in the plate 10 and helping to position the disc 50 relative to plate 10. Other ways of permanently fastening the plate 10 and disc 50 can be used instead of or in addition to the interference-fit, including adhesives and welding. The insert 50 makes it easier to accept manufacturing errors in the cavity 18, 18a and spring members 22, 22a since unacceptable parts can be discarded without causing the entire fixation plate 10 to be discarded.

As illustrated in FIG. 26, the disc 52 is inserted into a cylindrical structure containing step 56, inclined sidewall 58 and recess 60 which are representative of plate 10. This cylindrical structure, with disc 52 inserted into it, could in turn have a slightly tapered outer surface suitable for being press-fit, adhered, welded or otherwise permanently, or at least securely, fastened to a socket 80 (FIGS. 17-25) in plate 10.

Thus, the disc 50 could be press-fit (or otherwise fastened) into an insert which is in turn press-fit (or otherwise fastened) into a socket 80 in plate 10 or other suitable portion of plate 10. Thus, the assembly shown in FIG. 26 could have its outer periphery secured directly and permanently to an end of leg 74, or it could be inserted into a ring-shaped structure on the end of leg 74 to complete the formation of the socket 80.

Figure 18:
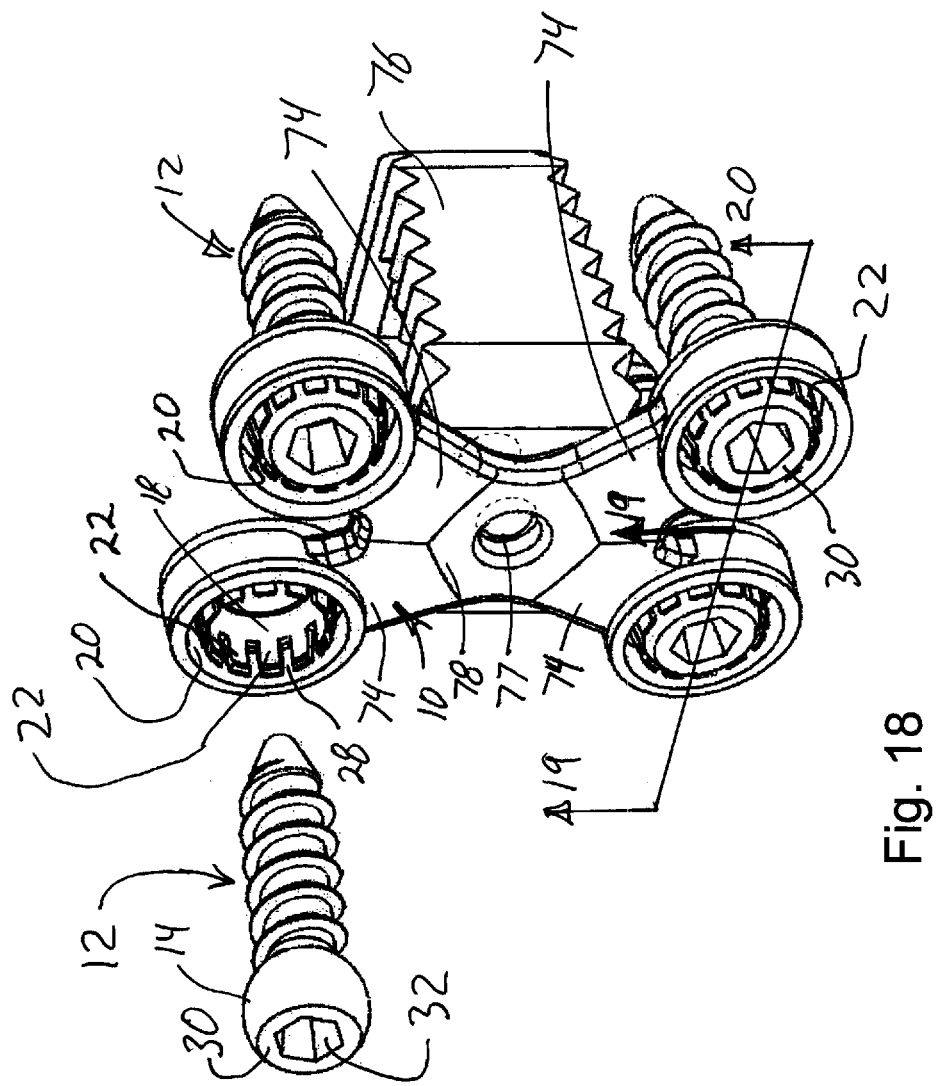
FIG. 18 is a perspective view of a spinal fixation plate with an X shape and four cavities containing the screw retention mechanisms of this invention, with three screws inserted and one screw as shown in FIG. 1 removed.
Figure 21:
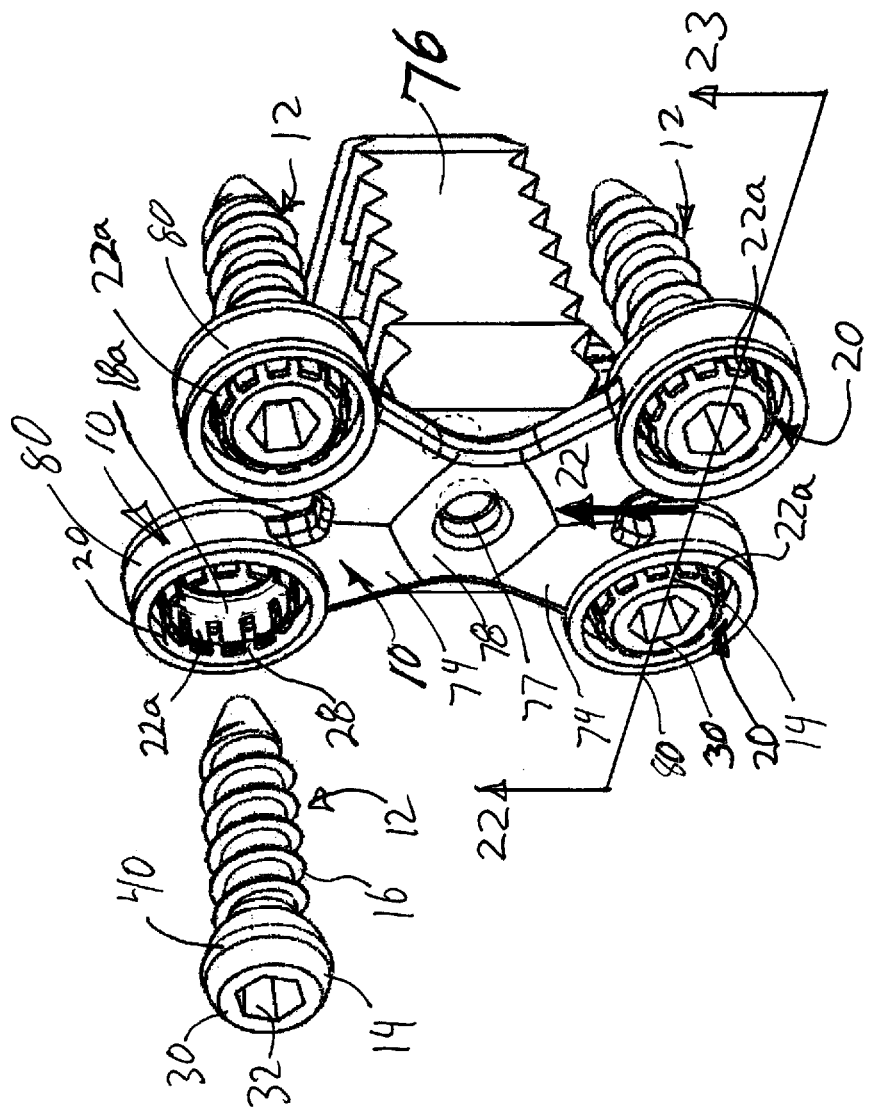
FIG. 21 shows a spinal fixation plate with an X shape and four cavities containing the screw retention mechanisms of FIG. 9, with one screw removed.
Figures 22, 23:
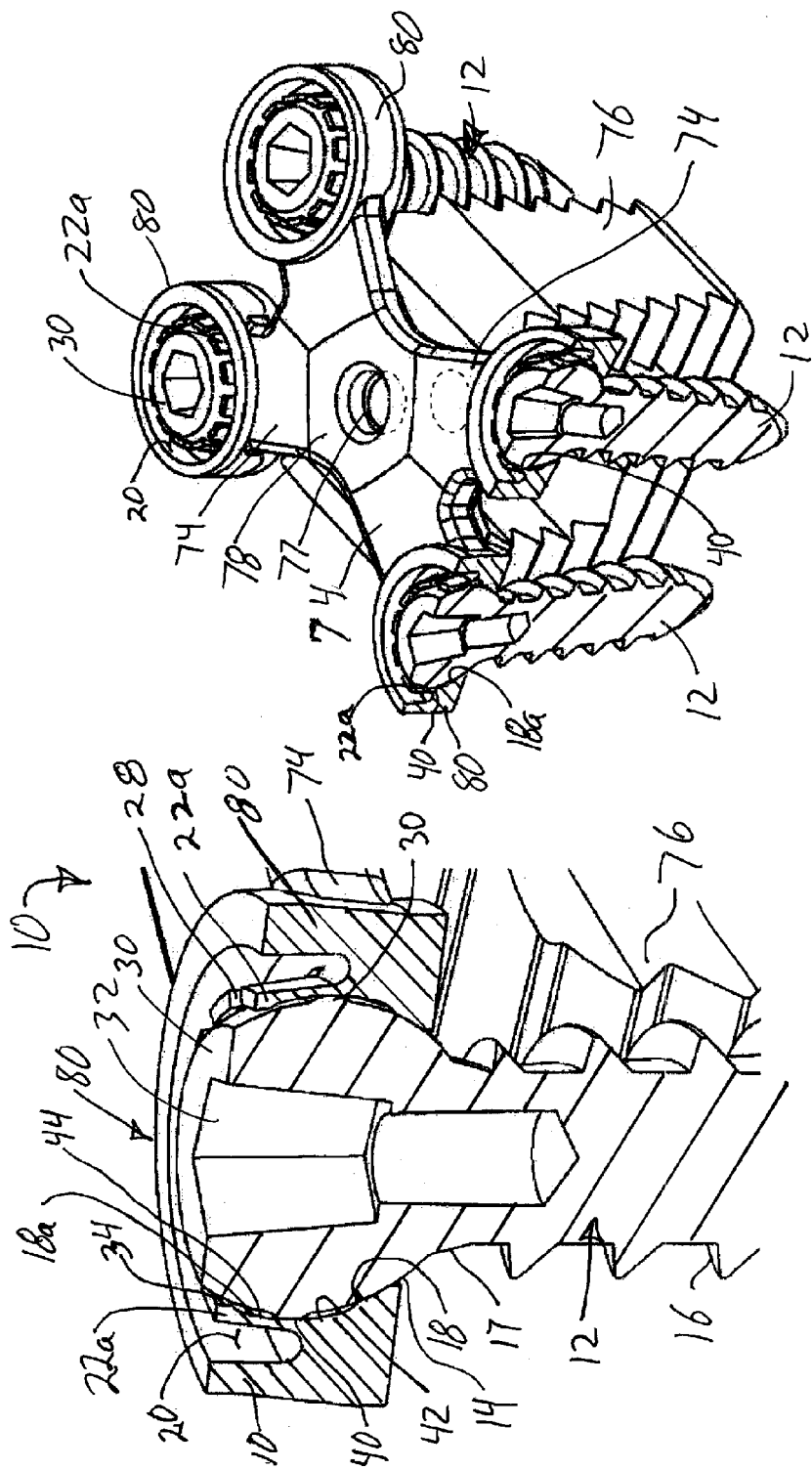
FIG. 22 is a partial perspective sectional view along 22-22 of FIG. 21.
FIG. 23 is a sectional view along 22-23 of FIG. 21.

Referring to FIGS. 18-20, the spring members may be used with plates 10 of varying shapes which plates include the spring members 22, 22a disclosed above. For illustration, an X-shaped plate is shown having four legs 74 and sockets for receiving screw heads 14 of bone screws 12 in cavities 18, 18a, the opening of which is surrounded by spring members 22, 22a. The sockets 80 can be used on plates 10 configured to extend across plural vertebrae, such that the plates have four, eight, twelve or sixteen sockets 80 with corresponding spring members 22, 22a, cavities 18, 18a and screws 14. Thus, the plates 10 preferably have at least four sockets 80 and associated spring members 22, 22a and cavities 18, 18a.

A vertebral body replacement 76 is fastened to the plate 10 and fits between adjacent vertebrae. The vertebral body replacement 76 is optional. Moreover, the fixation plate may or may not have a mount for the vertebral body replacement and may or may not have a graft attachment mount. The fixation plate 10 is believed suited for use with cervical vertebrae C2 through T1, and is believed especially suitable for C5-C6 fixation. This is referred to as a one-level fixation plate fixing two adjacent vertebrae and one intervening disc.

The bone screw 12 is made of stainless steel, titanium or other material of suitable strength and compatibility with implantation in the body. The wrenching socket 32 is preferably hexagonal in shape. Titanium alloy Ti-6A1-4V is believed suitable.

The X-shaped fixation plate 10 is preferably angled or curved slightly about two perpendicular axes to better conform to the local spinal shape. Thus, two sockets 80 on opposing sides of the cross-member 78 are bent slightly in the same anterior direction so the cross-member 78 is at the apex of a slightly V-shaped plate. As used herein "bent" does not mean the part is formed straight and then bent, but instead is used to refer to a direction as in the direction in which the part is bent or is inclined. Alternately described, the sockets 80 on opposing sides of the cross-member 78 are bent or inclined relative to the axial plane extending between adjacent, joined vertebrae and extending through the cross-member 78. The sockets 80 on the superior side of cross-member 78 are inclined slightly toward the sockets 80 on the inferior side of the cross-member and vice-versa. The sockets 80 and legs 74 are inclined at an angle □ of about 6° and possibly greater relative to a plane parallel to the coronal plane through the posterior of the cross-member 78. Inclination angles from 0° to about 12° are believed usable. The inclination angle □ is selected to conform to the curvature of the cervical vertebrae. The angle can vary depending on which vertebrae are joined by the fixation plate 10, and depending on whether an average curvature is used or on whether variations are made to accommodate an individual's specific spinal curvature. Preferably, the fixation plate 10 is made according to a predetermined curvature such as the average spinal curvature, with the plate being custom bent into a final shape that is based on X-rays of the spinal curvature of a specific user.

Two sockets 80 extend from each opposing end of cross-member 78 and those pairs of sockets are also inclined at an angle α, with an angle of about 6° also believed suitable. The cross-member 78 bends at its middle about the sagittal plane in an anterior direction so the two sockets on each end of the cross-member 78 are anterior of the middle of the cross-member 78. This slight curvature α allows the sockets 80 to better conform to the shape of the vertebrae and provides a lower profile for the fixation plate. Thus, relative to intersecting sagittal and axial planes which advantageously intersect at the center of the cross-member 78 of each X-shaped plate 10, each socket leg 74 and each socket 80 is inclined at an angle of about 6° relative to both the sagittal and axial planes. The center of the cross-member 78 forms an apex and that apex is preferably flattened slightly as described below to achieve a lower profile fixation plate and to allow the plate to fit below the muscle and tissue covering the posterior of the spine.

The center of the X-shaped fixation plate, at the center of the cross-member 78 (the apex), may have a hole 77 through the cross-member. A connector or mounting bracket 78 is formed on the plate 10 on the side of the cross-member 78 facing the spine during use. The hole may extend through the cross-member 78.

The X-shaped fixation plate 10 is believed to be suited for use with cervical vertebrae C2 through T1 and especially suitable for C5-C6. As such, the fixation plate 10 advantageously curves or angles to form a slightly concave plate facing the vertebrae to receive the vertebrae. The fixation plate 10 has a convex surface facing posterior, away from the vertebrae to reduce the height of the plate and to better conform to the vertebrae shape. Opposite the mounting bracket or cross-member 78, on the posterior side of the plate 10 facing away from the vertebrae during use, is a flattened portion 82. The flattened portion helps lower the height profile of the fixation plate 10. The flattened portion 82 may have a shape resembling a double headed arrow with flat tips on each arrow, and extending along the cross-member 78, especially when used with the X-shaped fixation plate 10 where the flattened portion extends onto portions of the legs 74 adjoining the cross member 78.

Since the legs 74 are inclined relative to the axial and saggital planes so the legs are angled toward the vertebrae in two axes, the flattened portion 82 is located at what would be the apex of the four inclined legs and reduces the height of that apex. The shape of flattened portion 82 depends on the inclination angle of the legs 74, and in this embodiment the tips of the arrow shape are at the ends of the cross-member 78, and the corners of the arrowhead are at the intersection of the legs 74 and the cross-member 78 near hole 77. The flattened portion 82 is, as the name implies flat, but could also be slightly inclined toward the location of the hole 77 at which the vertebral body replacement 76 attaches to the plate 10. A slightly curved surface could also be used and is considered encompassed within the meaning of a flattened surface. A similar flattened portion is formed on the opposing anterior side of the fixation plate 10. The similar flattened portion is generally like the flattened portion 82 except on the opposite side of the plate 10. A threaded fastener (not shown) can extend through the hole 77 and into the vertebral body replacement 76 to further secure the parts together. As desired, adhesives can be placed between the larger end replacement 76 and fixation plate 10 to also hold the parts together.

Referring to FIGS. 17-23, the spring members 22, 22a encircle the passage through each socket and its associated cavity 18, 18a. A screw 12 is passed through the spring members 22, 22a until the screw head 14 seats in the cavity 18, 18a. The screw head 14 abuts the inner wall of the cavity 18, 18a and of the spring members 22, 22a, with the spring members 22, 22a restraining removal of the screw 12. The spring members 22, 22a are sized so the head 14 of the screw 12 cannot expand the spring members enough to allow the head to pass through the spring members.

During insertion of the screw 12, the lower portion of screw head 14 adjacent tapered neck 17 abuts the inclined portions 34 on the free ends of spring members 22, 22a and pushes the spring members resiliently outward. The slots 28 allow each spring member 22, 22a to act as a leaf spring and to move as the head 14 passes. As the top edge 30 on the head 14 passes the spring members are resiliently urged inward to latch over the top edge 30 and restrain the screw head 14 and the screw 12 from being removed from the socket 80. Because the socket 80 is angled about 6° or more along two separate and perpendicular planes passing through the center of the X-shaped fixation plate, the screws 12 are also inclined. Such screws are known in the art.

Still referring to FIGS. 17-23, the screw head 14 and spring members 22, 22a cooperate with the cavity 18, 18a to allow the screw to rotate to any position within a cone around the longitudinal axis 26 through the cavity 18, 18a with the half angle □ of the cone being about 6° as seen in FIGS. 3, 6, 11 and 14. The shaped (preferably spherical) bearing surface on the screw head 14 abuts against mating (preferably spherical) inner surface of the cavity 18, 18a of to allow that rotation. The amount of rotation is limited because as the screw 12 tilts the top edge 30 and abuts the underside of the spring members 22, 22a, pushing up on select segments and causing the spring members to resist and limit further rotation. This rotation allows for adjustment and positioning of the fixation plate 10 and screws 12 during fastening, and allows some movement during use, both of which can be beneficial.

By forming the spring members 22, 22a integral with the fixation plate 10 and socket 80, intervening bushings are eliminated, thus providing more accurate control of position, along with more accurate control of the connection's stiffness and flexibility. The spring members 22, 22a provide resistance to back-out of the screw, yet also allow easy access to the socket 32 to remove the screw if needed, and further allow use of a simple removal tool shaped to match the socket.

During use, an intra-vertebral disc is removed between adjacent vertebrae. The vertebral body replacement 76 is selected to replace the disc and is either inserted between the vertebrae and then fastened to the fixation plate 10, or fastened to the plate 10 and then inserted between vertebrae. The fixation plate 10 is placed in position on the spine so that two sockets 80 overlap each vertebra. If the bone screws 12 are not self tapping, a hole is drilled though a socket 80, the hole is threaded and the screw is then threaded through the socket into the drilled hole. The process is repeated for the other sockets and screws, with any of various tightening sequences being used to seat the screws and affix the plate 10 to the vertebrae. If the screws 12 are self-tapping a pilot hole can be pre-drilled and the screws inserted through the bushings and screwed into place. The installation tool for the screws 12 has a wrenching surface configured to engage the wrenching socket 32 on the screw 12, and in the depicted embodiment has a hexagonal shape fitting into the hexagonal socket 32 in the head 14 of the screw.

As each screw 12 is seated the distal ends of spring members 22, 22a spread apart to allow passage of the screw head 14 which is larger than the opening defined by the spring members, with the spring members resiliently urged over the top edge 30 to restrain the screw from being removed. Advantageously the parts are sized so that the flanges 24 abut the curved surface of the head 14 to resiliently urge the screw toward the bone into which the screw is fastened during use. Alternatively, the flanges can be configured to extend over the top 30 and remain abutting the top edge 30 after the screws 12 are installed. The spring members 22, 22a allow the screw 12 to be inclined during installation, thereby making installation easier and accommodating misalignments. During maximum inclination of the screw 12 it is believed that about ⅓ of the spring members 22, 22a will abut the top edge 30 of the screw 12. The number of engaged spring members 22, 22a will vary with the number of spring members, which can vary as discussed herein. This same installation procedure or slight variations thereof can be used for the various embodiments of the fixation plate disclosed herein.

Because the spring members 22, 22a exert a resilient force on head 14, it is not believed necessary that the distal ends of the spring members have hooks or flanges that must engage the flat 30 of the edge formed by the juncture of the flat and spherical surface of spring head 14. Such hooking engagement with the flat 30 is, however, optional. The spring member 22, 22a resiliently urge the bone screw 12 toward the engaged vertebrae with sufficient force to prevent the screws from backing out. A resilient force of about 10-20 pounds per set of spring members 22, 22a is believed suitable, with a socket 80 having about 8-12 spring members, is believed sufficient, so each spring member 22, 22a preferably exerts a force of about 1-2 pounds against the curved head 14 of the screw 12. Yet the wrenching socket 32 allows a greater rotational force to be applied to the screw and back it out as needed. This type of engagement would eliminate the risk associated with having the thinner distal ends of spring members 22, 22a break off during installation or use.

Thus, the curved surface on spring members 22, 22a facing screw head 14 preferably joins flat, annular surface 36 or outwardly inclined surface 34 rather than surfaces forming a hooked end. In installation and use, as seen in FIGS. 4-5, the annular surface 36 is generally parallel to or only slightly inclined relative to longitudinal axis 26. One end (inner end) of that annular surface 36 intersects the curved engaging surfaces of the spring members 22, 22a which are inclined toward the axis 26 to intersect above the screw head 14. The other end (outer end) of that annular surface 36 intersects the conical, tapered surface 36 which is inclined along axes that intersect the longitudinal axis 26 in the head 14 or body of the screw 12.

Advantageously, the curved surfaces 14, 18 and 18a all have the same center of curvature during sue, and are preferably all spherical, so the parts rotate easily without lateral or axial displacement. The legs 74 and cross-member 78 are sized to allow a desired stiffness in the fixation plate parallel to and perpendicular to the legs, and also in the orthogonal plane toward and away from vertebrae. The legs 74 also allow some flexibility compared to a solid rectangular plate. The legs 74 are slightly angled to allow the fixation plate 10 to fit closer to the vertebrae and to conform to the local shape of the spine. The legs 74 are thin, preferably less than 2 mm thick. Advantageously, the fixation plate 10 does not extend more than about 2 mm above the adjacent vertebrae at the middle adjacent hole 77. Because the legs 74 are inclined about the saggital and axial planes, the legs and socket 80 can be slightly thicker. The end of vertebral replacement body 76 abutting plate 10 may be shaped to mate with the similar flattened portion on the underside of fixation plate 10, and the cooperating shapes preferably allow a slight rocking motion of the plate 10 and vertebral body 76 along an axis parallel to cross member 78, to allow a slight amount of flexibility in the assembly. The rocking is limited by contact between the plate 10 and replacement body 761.

The fixation plate 10 is made of suitably strong bio-compatible material, such as titanium, a suitable stainless steel, a nitinol or epoxy resin, or other appropriate composition suitable for the specific component. Titanium alloy Ti-6A1-4V is believed suitable. Other suitable materials now in existence or developed hereinafter can be used for the various parts herein.

The above description is given by way of example, and not limitation. Given the above disclosure, one skilled in the art could devise variations that are within the scope and spirit of the invention disclosed herein, including various ways of shaping or configuring the spring members 22, 22a. Further, the various features of the embodiments disclosed herein can be used alone, or in varying combinations with each other and are not intended to be limited to the specific combination described herein. Moreover, the mechanism for retaining the bone screw 14 is described for use in a spinal fixation plate 10, but the use need not be so limited as the spring members 22, 22a, cavities 18, 18a, screw 14 and associated parts could be used in other bone fixation or bone stabilization applications. Thus, the scope of the claims is not to be limited by the illustrated embodiments.

What is claimed is:

1. A bone fixation apparatus in which a threaded fastener passes through a hole in a plate and into a bone to affix the bone to the plate during use, the bone fixation apparatus comprising:
    a plate having a hole extending through the plate, the plate having top and bottom surfaces on opposing sides of the plate with the hole having a circular opening on both surfaces and with the bottom surface being adjacent to the bone during use, the openings having a longitudinal axis through the center of the openings, the hole having a portion of at least a first spherical cavity therein centered on the longitudinal axis,
    a plurality of resilient spring members integrally formed as an inseparable part with the plate and encircling the opening on the top surface, an annular groove in the plate centered on the longitudinal axis and extending a distance into the plate to define a length of the spring members and an outer surface of the spring members facing away from the longitudinal axis, a plurality of slots in the plate extending into the plate about the length of the spring members to define sides of the spring members, an inner side of the spring members facing the longitudinal axis having a curved surface defining a portion of the first cavity, the spring members configured to move resiliently outwards away from the longitudinal axis to allow a portion of the fastener to be positioned in the opening, and configured to move resiliently inwards after insertion of a portion of the fastener to resist removal of the fastener from the plate until the resistance of spring members is overcome.

2. The apparatus of claim 1, further comprising a fastener having a spherical portion on a head of the fastener and having a spherical diameter about the same as that of the cavity or slightly smaller.

3. The apparatus of claim 1, wherein the inner and outer sides of the spring members are curved with the curves being concentric about the longitudinal axis.

4. The apparatus of claim 1, wherein the cavity has a diameter d and the spring members define about half of that cavity.

5. The apparatus of claim 1, wherein the spring members have an outer surface each of which forms a portion of a cone centered about the longitudinal axis.

6. The apparatus of claim 5, wherein the spring members are formed on a disc having a cone shape coincident with the conical surface on the outer surface of the spring members, the disc having an outwardly extending flange at the bottom surface of the plate.

7. The apparatus of claim 1, wherein a distal end of each spring member has a first annular surface oriented to urge the spring members away from the longitudinal axis when the head of a screw passes into the cavity along the longitudinal axis.

8. The apparatus of claim 7, further comprising a second annular surface adjoining the first annular surface and oriented to be generally aligned with the longitudinal axis as the largest portion of a fastener passes the second surface.

9. The apparatus of claim 1, wherein the inner side of the spring members further define a second cavity having a larger diameter than the first cavity, the second cavity extending into the plate below the spring members.

10. The apparatus of claim 9, further comprising a threaded fastener having a spherical head with a ring extending outward from that spherical head, the ring sized to fit in the second cavity during use.

11. The apparatus of claim 1, wherein the plate comprises an X-shaped spinal fixation plate having four legs with a socket at a distal end of each plate, each socket having the defined fixation plate.

12. The apparatus of claim 1, wherein the inner side of the spring members further define a second cavity having a larger diameter than the first cavity, the second cavity extending into the plate below the spring members and having spherically curved walls.

13. The apparatus of claim 1, wherein the spring members are formed from the same piece of material as the plate.

14. The apparatus of claim 1, wherein the spring members made separately as an insert that is placed into a cavity in the plate and then permanently secured to the plate.

15. A bone stabilization system, comprising:
a plate having a top and bottom surface, the plate having a hole therethrough extending along a longitudinal axis of the hole, the top surface of the plate having an annular groove centered on the longitudinal axis and extending into the plate a distance sufficient to define outer facing sides of a plurality of spring members integral to the plate so as to be immovably connected to the plate, the plate having a plurality of slots defining sides of the spring members, the hole inside the plate having walls defining at least a portion of a first spherical cavity with a diameter d centered on the longitudinal axis, an inward facing surface of the spring members defining an upper portion of the first cavity and distal ends of the spring members defining a top opening to the cavity in the top surface of the plate, the plate below the spring members defining a lower portion of the first cavity;
a fastener positionable through the top opening, the fastener including a head, and wherein the spring members are configured to be resiliently urged against a curved portion of the head to resist removal of the fastener from the plate during use until the resistance provided by the spring members is overcome.

16. The apparatus of claim 15, wherein the inward and outward facing sides of the spring members are curved concentric with the longitudinal axis.

17. The apparatus of claim 16, wherein the outer facing sides of the spring members form a portion of a conical surface having an apex on the longitudinal axis and located above the plate during use.

18. The apparatus of claim 15, wherein the inward facing surface of the spring members define a portion of a sphere with a diameter of about d.

19. The apparatus of claim 15, wherein the annular groove has a curved bottom, with the slots extending to about the bottom of the groove.

20. The apparatus of claim 15, wherein the hole in the plate further comprises a second cavity extending into the walls defining the first cavity and having a diameter D larger than the diameter d.

21. The apparatus of claim 20, wherein the screw includes a head with a portion of a sphere and an outwardly extending ring on that spherical portion having a diameter of about D.

22. The apparatus of claim 15, wherein the spring members each have a distal end forming a first annular surface inclined to intersect the longitudinal axis below the top surface of the plate during use.

23. The apparatus of claim 22, wherein the distal ends of the spring members define a second annular surface adjoining the first annular surface and inclined to intersect the longitudinal axis above the top surface of the plate.

24. The apparatus of claim 15, wherein the spring members are formed from the same piece of material as the plate.

25. The apparatus of claim 15, wherein the spring members made separately as an insert that is placed into a cavity in the plate and then permanently secured to the plate.

* * * * *